United States Patent
Bodas et al.

(10) Patent No.: US 11,865,533 B2
(45) Date of Patent: Jan. 9, 2024

(54) PROGRAMMABLE LOGIC CONTROLLER FOR DEHYDROGENATION PROCESS WITH REDUCED HOUDRY LUMPS

(71) Applicant: SABIC GLOBAL TECHNOLOGIES B.V., Bergen op Zoom (NL)

(72) Inventors: Vijay Dinkar Bodas, Riyadh (SA); Guillermo Leal Canelon, Riyadh (SA); Mohammed Bismillah Ansari, Riyadh (SA)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 316 days.

(21) Appl. No.: 17/435,451

(22) PCT Filed: Mar. 10, 2020

(86) PCT No.: PCT/IB2020/052053
§ 371 (c)(1),
(2) Date: Sep. 1, 2021

(87) PCT Pub. No.: WO2020/183359
PCT Pub. Date: Sep. 17, 2020

(65) Prior Publication Data
US 2022/0055002 A1    Feb. 24, 2022

Related U.S. Application Data

(60) Provisional application No. 62/817,931, filed on Mar. 13, 2019.

(51) Int. Cl.
*B01J 8/02* (2006.01)
*B01J 8/00* (2006.01)
(Continued)

(52) U.S. Cl.
CPC ............ *B01J 8/0278* (2013.01); *B01J 8/001* (2013.01); *B01J 19/002* (2013.01);
(Continued)

(58) Field of Classification Search
CPC ........ B01J 8/0278; B01J 8/001; B01J 19/002; B01J 19/2445; B01J 2219/00072; C07C 5/327; G05B 19/05; G05B 2219/15052
See application file for complete search history.

(56) References Cited

U.S. PATENT DOCUMENTS 3,937,747 A * 2/1976 Thornton ................ C07C 5/333
585/501
4,754,094 A * 6/1988 Jubin, Jr. ................. C07C 5/48
585/656
(Continued)

FOREIGN PATENT DOCUMENTS

CN    106478351    2/2019
SU    1357408    12/1987
(Continued)

OTHER PUBLICATIONS

Acrivos et al., "Flow distributions in manifolds," *Chemical Engineering Science*, 1959, 10(102):112-124.
(Continued)

*Primary Examiner* — Ali Z Fadhel
(74) *Attorney, Agent, or Firm* — Norton Rose Fulbright US LLP

(57) ABSTRACT

Houdry lumps can be reduced by controlling the reactors in a fixed bed dehydrogenation process for producing olefins according to defined rules. A programmable logic controller can apply the rules to the operation of the dehydrogenation unit and control the operation of individual reactors according to the rules. By doing so, the performance of dehydrogenation units can be improved without adding any heat
(Continued)

generating inerts, such as CuO-α alumina For example, the dehydrogenation units can be operated according to combinatorics in the programmable logic controller such that the farthest two reactors in the dehydrogenation unit never operate in parallel in the dehydrogenation or air regeneration steps.

20 Claims, 2 Drawing Sheets

(51) Int. Cl.
    *B01J 19/00* (2006.01)
    *B01J 19/24* (2006.01)
    *C07C 5/327* (2006.01)
    *G05B 19/05* (2006.01)

(52) U.S. Cl.
    CPC ........ *B01J 19/2445* (2013.01); *C07C 5/327* (2013.01); *G05B 19/05* (2013.01); *G05B 2219/15052* (2013.01)

(56) References Cited

U.S. PATENT DOCUMENTS

| | | | |
|---|---|---|---|
| 4,789,528 A * | 12/1988 | Owen | B01J 8/0488 422/223 |
| 4,996,387 A * | 2/1991 | Gerhold | C07C 5/325 208/138 |
| 10,017,431 B2 * | 7/2018 | Schwint | C07C 5/333 |
| 11,124,467 B2 * | 9/2021 | Takahashi | C07C 17/25 |
| 2004/0015012 A1 | 1/2004 | Hammon et al. | |
| 2004/0087825 A1 | 5/2004 | Urbancic et al. | |
| 2006/0106269 A1 * | 5/2006 | Culp | B01J 8/025 585/444 |
| 2020/0179892 A1 * | 6/2020 | Lattanzio | B01J 8/0015 |
| 2022/0048833 A1 * | 2/2022 | Drobyshev | B01J 19/14 |

FOREIGN PATENT DOCUMENTS

| | | |
|---|---|---|
| SU | 1527231 | 12/1989 |
| WO | WO 2018/172889 | 9/2018 |
| WO | WO 2018/203233 | 11/2018 |

OTHER PUBLICATIONS

International Search Report and Written Opinion issued in Corresponding PCT Application No. PCT/IB2020/052053, dated May 12, 2020.

* cited by examiner

PROGRAMMABLE LOGIC CONTROLLER FOR DEHYDROGENATION PROCESS WITH REDUCED HOUDRY LUMPS

CROSS REFERENCE TO RELATED APPLICATIONS

This application is a national phase under 35 U.S.C. § 371 of International Application No. PCT/IB2020/052053, filed Mar. 10, 2020, which claims the benefit of priority of U.S. Provisional Patent Application No. 62/817,931, filed Mar. 13, 2019, each of which are hereby incorporated by reference in their entirety.

FIELD OF INVENTION

The present invention generally relates to process control for chemical production units. More specifically, the present invention relates to programmable logic controllers for fixed bed dehydrogenation units.

BACKGROUND OF THE INVENTION

Fixed bed dehydrogenation units are used for on-purpose production of olefins and/or alkynes from alkanes and/or olefins. Generally, a fixed bed dehydrogenation unit comprises three or more parallel fixed bed reactors and a catalyst regeneration system. When the fixed bed dehydrogenation unit is in operation, one or more reactors are on line (in dehydrogenation mode), and one or more fixed bed reactors are in regeneration mode. Additional fixed bed reactors might be in standby mode. A fixed bed reactor in dehydrogenation mode first dehydrogenates the hydrocarbon feed for a period of time. Then, the fixed bed reactor can be purged with steam. In a subsequent regeneration mode, heated air can be blown through to decoke the catalyst disposed in the fixed bed reactor. The reactor can in turn be evacuated and the catalyst in the reactor can undergo reduction. After catalyst reduction, the reactor can be placed back on line for dehydrogenation reactions. The same sequence can be repeated automatically for each fixed bed reactor using a programmable logic controller (PLC) to ensure continuous production of the entire dehydrogenation unit.

Commercial programmable logic controllers often employ simplified algorithms to program the fixed bed dehydrogenation units with an inflexible and conservative approach. A conventional manifold design for sequencer controlled multiple fixed bed adiabatic dehydrogenation based olefin manufacture is shown in FIG. 1, which includes five example reactors 102A-E. Of these reactors 102A-E operating in tandem, any two (or less than all) may be online in dehydrogenation, whereas the others may be in air regeneration or in some other step of a regulated sequence. However, operation of a reactor according to these conventional techniques can result in formation of what are known as Houdry lumps. These are stalagmite like structures of alpha chrome alumina formed by catalyst conversion to (almost) synthetic rubies, rising as mounds growing from bottom towards the top in the catalyst bed. One conventional technique for dealing with Houdry lumps is killing off the catalyst in a lower part of the bed by incorporating heat generating inert materials loaded in an upper section of the bed. One issue with these heat generating inerts is that they can release water during their redox cycle between dehydrogenation and air regeneration. This water can pass over the lower portion of the catalyst bed, effectively killing the catalytic bed. While this reduces the Houdry lumps, it gives rise to a situation where a significant portion of lower catalyst bed is killed off. This reduces productivity during the aging process of catalyst operational life.

BRIEF SUMMARY OF THE INVENTION

The conventional operation of reactors in a fixed bed dehydrogenation unit are used for on-purpose production of olefins and/or alkynes from alkanes and/or olefins. Conventional operation gives rise to a systematic deviation of flow between the reactors. That is, particular reactors undergo more aging of catalyst or undergo more air regeneration or heating up compared to other reactors. These deviations are found to be a contributing factor in the creation of the undesirable Houdry lumps. A solution to this problem has been discovered in the context of the present invention. According to embodiments of the present invention, the Houdry lumps can be reduced by controlling the reactors in the dehydrogenation unit according to defined rules. A programmable logic controller can apply the rules to the operation of the dehydrogenation unit and control the operation of individual reactors according to the rules. By doing so, the performance of dehydrogenation units can be improved without adding any heat generating inerts, such as $CuO$-$\alpha$ alumina.

In one example embodiment, the dehydrogenation units can be operated according to combinatorics in the programmable logic controller such that the farthest two reactors in the dehydrogenation unit never operate in parallel in the dehydrogenation or air regeneration steps. The programming of the programmable logic controller can be done off line, during shutdown of an existing unit, or during first construction of the unit. This rule regarding the farthest two reactors not operating in parallel in dehydrogenation or air regeneration reduces flow imbalance between any two reactors of the system, which consequently reduces the heat input and withdrawal differences between any two reactors. This results in reduced formation of Houdry lumps in specific reactors that are exposed to systematic thermal imbalance that would otherwise occur without the application of this rule during operation of the programmable logic controller. This thermal imbalance would otherwise result in the damage of the catalyst used for dehydrogenation. Examples of dehydrogenation processing that can implemented using such a rule include propane dehydrogenation, isobutane dehydrogenation, n-butane to butene-1 and subsequently butadiene and isopentane dehydrogenation processes.

Average quantity of Houdry lumps in conventionally-operated reactors can be greater than 3000 kg when taken out during shutdown when not using heat generating inerts to kill the lower bed catalyst. When the reactors are operated with the controller-based rule of the present invention, the quantity of Houdry lumps can be 3000 kg or less, preferably 2500 kg or less, or more preferably about 200 kg to 2000 kg, 200 kg to 500 kg, 200 kg to 400 kg, or about 250 kg to about 350 kg. These values can be measured in relation to a loaded mixture of catalyst weight of 85000 kg and 85000 kg of inert Alumina grains in a single reactor. These results can be achieved when not using heat generating inerts.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %," or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification. With respect to the phrase "consisting essentially of," a basic and novel characteristic of the present invention is the reduction of the size and/or formation of Houdry lumps when the farthest two reactors in the dehydrogenation unit never operate in parallel in the dehydrogenation or air regeneration steps.

In the context of the present invention, at least twenty embodiments are now described. Embodiment 1 is method of performing a fixed bed dehydrogenation process for producing olefins. The method includes the steps of controlling at least three fixed bed dehydrogenation reactors configured to dehydrogenate a hydrocarbon to produce an olefin, wherein the controlling is performed such that a farthest two of the reactors, by distance, from each other are not operated simultaneously in either of dehydrogenation processing and catalyst regeneration processing. Embodiment 2 is the method of embodiment 1, wherein two or more of the reactors are allowed to be in the dehydrogenation processing and catalyst regeneration processing phases in parallel, as long as the two farthest reactors are not in parallel. Embodiment 3 is the method of any one of embodiments 1-2, wherein the number of reactors is 3, 4, 5, 8, or 10. Embodiment 4 is the method of any one of embodiments 1-3, wherein the dehydrogenation processing is a propane dehydrogenation process. Embodiment 5 is the method of embodiment 4, wherein the number of reactors are 8 or 10. Embodiment 6 is the method of any one of embodiments 1-3, wherein the dehydrogenation processing is an isobutane dehydrogenation process, a n-butane to butene-1 dehydrogenation process, or a butadiene or isopentane dehydrogenation process. Embodiment 7 is the method of embodiment 6, wherein the number of reactors are 3, 4, or 5. Embodiment 8 is the method of any one of embodiments 1-7, wherein the method is performed without heat generating inerts. Embodiment 9 is the method of any one of embodiments 1-8, wherein the method is performed without CuO-α alumina. Embodiment 10 is the method of any one of embodiments 1-9, wherein operation of the process results in Houdry lumps of 3000 kg or less, preferably 2500 kg or less, or more preferably about 500 kg to 2000 kg. Embodiment 11 is the method of any one of embodiments 1 to 10, wherein the size of Houdry lumps formed in the at least three fixed bed dehydrogenation reactors are reduced compared to a method of controlling that is performed such that the farthest two reactors, by distance, from each other are operated simultaneously in either of dehydrogenation processing and catalyst regeneration processing.

Embodiment 12 is a method of performing a fixed bed dehydrogenation process for producing olefins. The method includes the steps of controlling a multiple fixed bed adiabatic dehydrogenation based olefin manufacture system that comprises at least three fixed bed dehydrogenation reactors that are configured to share a feed source and configured to dehydrogenate a hydrocarbon to produce an olefin, wherein each of the at least three fixed bed dehydrogenation reactors comprise a catalyst bed that does not include a heat generating inert material, wherein the controlling is performed such that a farthest two of the reactors, by distance, from each other are not operated simultaneously in either of dehydrogenation processing and catalyst regeneration processing, and wherein the size of Houdry lumps formed in the at least three fixed bed dehydrogenation reactors are reduced compared to a method of controlling that is performed such that the farthest two reactors, by distance, from each other are operated simultaneously in either of dehydrogenation processing and catalyst regeneration processing. Embodiment 13 is the method of embodiment 12, wherein two or more of the reactors are allowed to be in the dehydrogenation processing and catalyst regeneration processing phases in parallel, as long as the two farthest reactors are not in parallel. Embodiment 14 is the method of any one of embodiments 12-13, wherein the number of reactors is 3, 4, 5, 8, or 10. Embodiment 15 is the method of any one of embodiments 12-14, wherein the dehydrogenation processing is a propane dehydrogenation process. Embodiment 16 is the method of embodiment 15, wherein the number of reactors are 8 or 10. Embodiment 17 is the method of any one of embodiments 12-14, wherein the dehydrogenation processing is an isobutane dehydrogenation process, a n-butane to butene-1 dehydrogenation process, or a butadiene or isopentane dehydrogenation process. Embodiment 18 is the method of embodiment 17, wherein the number of reactors are 3, 4, or 5. Embodiment 19 is the method of any one of embodiments 12-18, wherein operation of the process results in Houdry lumps of 3000 kg or less, preferably 2500 kg or less, or more preferably about 500 kg to 2000 kg. Embodiment 20 is a programmable logic controller configured to perform the method of any one of embodiments 1-19.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for dehydrogenating a hydrocarbon in a fixed bed dehydrogenation unit comprising one or more parallel fixed bed reactors. By implementing the method in the dehydrogenation unit, the Houdry lumps can be reduced, thereby improving the efficiency of the fixed bed dehydrogenation unit and reducing production cost without substantial capital expenditure. In some embodiments, the Houdry lump reduction can be achieved without using heat generating inerts to kill off the lower bed catalyst as in prior solutions.

Figure 1:
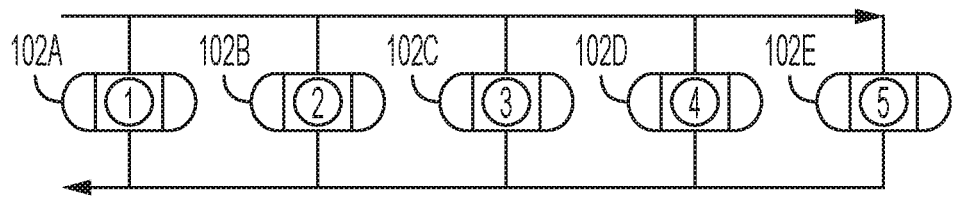
FIG. 1 shows a conventional reactor arrangement for fixed bed adiabatic dehydrogenation based olefin manufacture.
Figure 2:
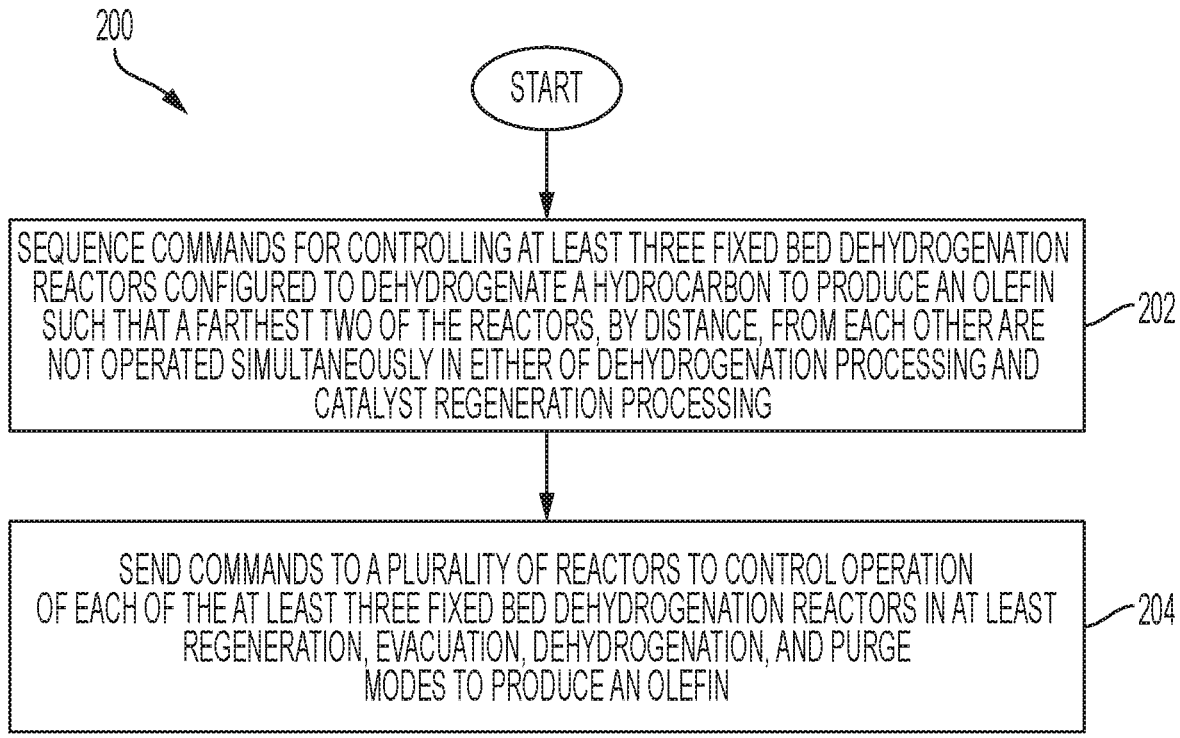
FIG. 2 shows a flow chart illustrating a method for controlling a fixed bed adiabatic dehydrogenation based olefin reactor system according to some embodiments of the disclosure.

FIG. 2 shows a flow chart illustrating a method for controlling a fixed bed adiabatic dehydrogenation based olefin reactor system according to some embodiments of the disclosure. A method 200 begins at block 202 with sequencing commands for controlling at least three fixed bed dehydrogenation reactors configured to dehydrogenate a hydrocarbon to produce an olefin such that a farthest two of the reactors, by distance, from each other are not operated simultaneously in either of dehydrogenation processing and catalyst regeneration processing. The sequencing may be performed by a processor or other logic circuitry in a programmable logic controller (PLC) coupled to control systems within each reactor. The sequencing of block 202 may include determining times to transition each of the reactors between at least regeneration, evacuation, dehydrogenation, and/or purge modes. The commands may be sequenced such that at no time during the sequencing would a farthest two of the reactors, by distance, from each other be operated simultaneously in either of dehydrogenation processing and catalyst regeneration processing. In some embodiments, two or more of the reactors are allowed to be in the dehydrogenation processing and catalyst regeneration processing phases in parallel, as long as the two farthest reactors are not operated in parallel.

After sequencing the commands by selecting modes and times for each of the at least three reactors, the commands may be sent to the reactors at block 204. The commands may be sequenced at block 202 and stored in memory available to the PLC to be later transmitted to reactors at the time that the reactor should transition between modes. For example, if the command sequence of block 202 includes a command to transition reactor 1 to dehydrogenation at time t1, such a command may be sent to reactor 1 at time t1. The commands may alternatively be transmitted to the reactor systems with a timing indication to indicate a time in the future that the reactor should transition between modes. For example, if the command sequence of block 202 includes a command to transition reactor 1 to dehydrogenation at time t1, such a command may be sent to reactor 1 in advance of time t1 at time t1-t2 with an instruction to transition at time t1. In this arrangement, a limited number of commands may be buffered at the reactors and executed at the appropriate time. Timing may be coordinated between the reactors using a shared clock signal, a remote time server, or other time synchronization signal.

Operation of the fixed bed dehydrogenation reactors as shown in FIG. 2 can reduce the amount of Houdry lumps occurring in the reactors. In particular, the size of Houdry lumps formed in the at least three fixed bed dehydrogenation reactors can be reduced compared to a method of controlling that is performed such that the farthest two reactors, by distance, from each other are operated simultaneously in either of dehydrogenation processing and catalyst regeneration processing. In these reactors, hydrocarbons enter from one end of the header and air enters from another header coming in from an opposite end. The reactor that has the highest airflow due to air maldistribution will have the lowest hydrocarbon flow due to maldistribution in the reactors. The reactors that experience higher gap between heat supply from air and endotherms from hydrocarbons are known to typically have larger amount of Houdry lumps. The operation of the reactors such that a farthest two of the reactors, by distance, from each other are not operated simultaneously in either of dehydrogenation processing and catalyst regeneration processing reduces this maldistribution and thus reduces the collection of Houdry lumps. Typical collection of Houdry lumps in conventional reactors weigh up to or more than 2000 kg or more than 3000 kg per reactor when taken out during shutdown when not using heat generating inerts to kill the lower bed catalyst. This method of reactor control described in FIG. 2 can reduce the quantity of Houdry lumps to 3000 kg or less, preferably 2500 kg or less, or more preferably about 200 kg to 2000 kg, 200 kg to 500 kg, 200 kg to 400 kg, or about 250 kg to about 350 kg. This reduction in Houdry lumps can be achieved without using heat generating inerts.

Figure 3:
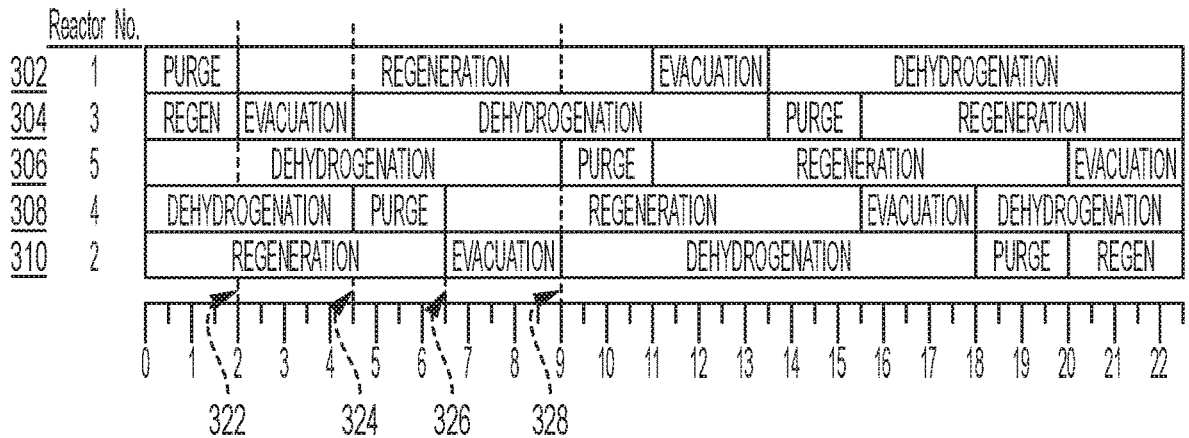
FIG. 3 shows an example reactor sequence for controlling a fixed bed adiabatic dehydrogenation based olefin reactor system to reduce Houdry lumps according to some embodiments of the disclosure.

An illustration of a command sequence for an example reactor system with five reactors according to the method of FIG. 2 is shown in FIG. 3. FIG. 3 shows an example reactor sequence for controlling a fixed bed adiabatic dehydrogenation based olefin reactor system to reduce Houdry lumps according to some embodiments of the disclosure. FIG. 3 shows timing sequences for reactors 302, 304, 306, 308, and 310. The reactors may be ordered first to last in a system as 302, 310, 304, 308, and 306. The reactors are sequenced by sending commands that cause, in this example, reactor 302 to transition from purge to regeneration at time 322. Also at time 322, reactor 304 transitions from regeneration to evacuation. At time 324, reactor 304 transitions from evacuation to hydrogenation and reactor 308 transitions from dehydrogenation to purge. At time 326, reactor 316 transitions from regeneration to evacuation and reactor 308 transitions from purge to dehydrogenation. At time 328, reactor 316 transitions from evacuation to dehydrogenation and reactor 306 transitions from dehydrogenation to purge. Other sequenced commands are shown in FIG. 3 in this example operation for five reactors 302, 304, 306, 308, and 310. In the sequencing of reactors 302, 304, 306, 308, and 310 no farthest two of the reactors, by distance, from each other are operated simultaneously in either of dehydrogenation processing and catalyst regeneration processing. The sequence of operation of reactors 302, 304, 306, 308, and 310 reduces, and may minimize, the maldistribution in the reactors.

In embodiments of the invention, hydrocarbons may be dehydrogenated in the presence of a catalyst in one or more of reactors 302, 304, 306, 308, and 310 for a period that may be in a range of 7 to 18 minutes, and all ranges and values there between including 7 to 8 minutes, 8 to 9 minutes, 9 to 10 minutes, 10 to 11 minutes, 11 to 12 minutes, 12 to 13 minutes, 13 to 14 minutes, 14 to 15 minutes, 15 to 16 minutes, 16 to 17 minutes, or 17 to 18 minutes.

Although FIG. 3 is an example for a five reactor system, the method of FIG. 2 may likewise be applied to systems with three, four, eight, ten, or other numbers of reactors. The command sequence may also depend on layout and direction of the reactors, and a programmable logic controller can be programmed with a configuration file or other settings indicating the reactor layout. The programmable logic controller may then adjust command sequences based on a particular reactor system configuration according to the method of FIG. 2 such that no farthest two of the reactors, by distance, from each other are operated simultaneously in either of dehydrogenation processing and catalyst regeneration processing. The method of reactor system control described herein may be applied to different types of processing, including propane dehydrogenation, isobutane dehydrogenation, n-butane to butene-1, and subsequently butadiene and isopentane dehydrogenation processes.

According to embodiments of the invention, reactors 302, 304, 306, 308, and 310 may be operated under reaction conditions that are different from each other, reaction conditions that are same as each other, or where a first set or the reactors is operated at a first set of reaction conditions and a second set is operated at a second set of reaction conditions (different from the first set of reaction conditions). The reaction conditions may include providing a particular catalyst for the dehydrogenation desired. In embodiments of the invention, the catalyst includes chromium oxide over alumina, tin-platinum over alumina and/or Chlorided platinum over aluminum. In embodiments of the invention, the reaction conditions may include reaction temperature, reaction pressure and weight hourly space velocity (weight flowrate of the feed divided by the catalyst weight), or combinations thereof. The reaction temperature may be in a range of 540° C. to 750° C. and all ranges and values there between including ranges of 540° C. to 550° C., 550° C. to 560° C., 560° C. to 570° C., 570° C. to 580° C., 580° C. to 590° C., 590° C. to 600° C., 600° C. to 610° C., 610° C. to 620° C., 620° C. to 630° C., 630° C. to 640° C., 640° C. to 650° C., 650° C. to 660° C., 660° C. to 670° C., 670° C. to 680° C., 680° C. to 690° C., 690° C. to 700° C., 700° C. to 710° C., 710° C. to 720° C., 720° C. to 730° C., 730° C. to 740° C., or 740° C. to 750° C., The reaction pressure may be in a range of 0.2 to 1.2 bar and all ranges and values there between including 0.2 bar, 0.3 bar, 0.4 bar, 0.5 bar, 0.6 bar, 0.7 bar, 0.8 bar, 0.9 bar, 1.0 bar, 1.1 bar, or 1.2 bar. The weight hourly space velocity may be in a range of 1 to 1.6 and all ranges and values there between including 1, 1.1, 1.2, 1.3, 1.4, 1.5 or 1.6.

According to embodiments of the invention, the regeneration processing includes regenerating conditions that can include a regenerating temperature of 400 to 900° C. and all ranges and values there between including ranges of 400 to 450° C., 450 to 500° C., 500 to 550° C., 550 to 600° C., 600 to 650° C., 650 to 700° C., 700 to 750° C., 750 to 800° C., 800 to 850° C., 850 to 900° C. The regenerating conditions can include a regenerating pressure of 0.1 to 10 bar and all ranges and values there between including ranges of 0.1 to 0.2 bar, 0.2 to 0.3 bar, 0.3 to 0.4 bar, 0.4 to 0.5 bar, 0.5 to 0.6 bar, 0.6 to 0.7 bar, 0.7 to 0.8 bar, 0.8 to 0.9 bar, 0.9 to 1 bar, 1 to 2 bar, 2 to 3 bar, 3 to 4 bar, 4 to 5 bar, 5 to 6 bar, 6 to 7 bar, 7 to 8 bar, 8 to 9 bar, and 9 to 10 bar. The regenerating conditions can include regenerating period that may be in a range of 7 to 18 minutes, and all ranges and values there between including 7 to 8 minutes, 8 to 9 minutes, 9 to 10 minutes, 10 to 11 minutes, 11 to 12 minutes, 12 to 13 minutes, 13 to 14 minutes, 14 to 15 minutes, 15 to 16 minutes, 16 to 17 minutes, or 17 to 18 minutes.

Figure 4:
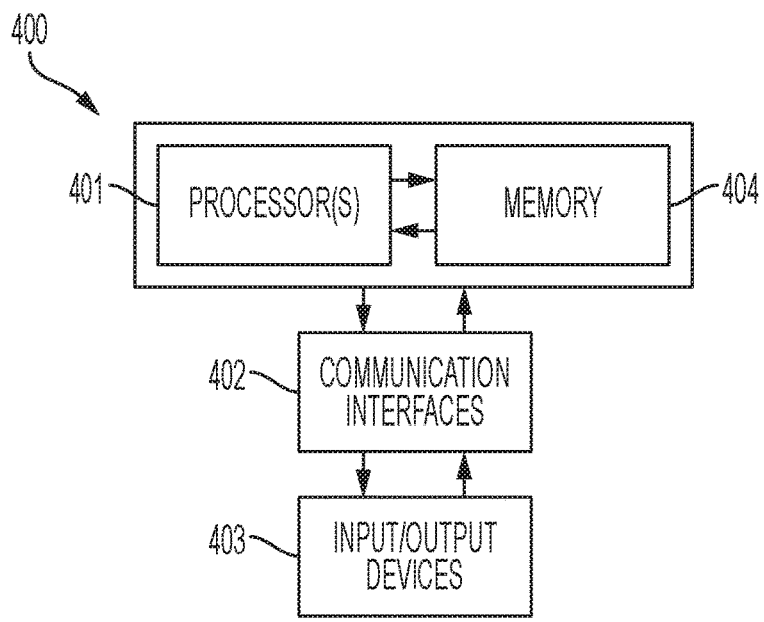
FIG. 4 is a block diagram illustrating a programmable logic controller for controlling a fixed bed adiabatic dehydrogenation based olefin reactor system according to some embodiments of the disclosure.

Embodiments of the invention provide a control system for controlling the reactors for a fixed bed adiabatic dehydrogenation based olefin reactor system. FIG. 4 is a block diagram illustrating a programmable logic controller for controlling a fixed bed adiabatic dehydrogenation based olefin reactor system according to some embodiments of the disclosure. As shown in FIG. 4, control system 400 may include one or more processors 401, one or more communication interfaces 402, one or more input/output devices 403, and memory 404. Although processors 401 are shown, the term processors should include any logic circuitry that can be configured to perform the control methods described herein. Thus, processors 401 may include different kinds of processors, such as graphics processing units (GPUs), central processing units (CPUs), and digital signal processors (DSPs), and other logic circuitry such as application-specific integrated circuits (ASICs). The memory 404 may include one or more random access memory (RAM) devices, read only memory (ROM) devices, one or more hard disk drives (HDDs), flash memory devices, solid state drives (SSDs), network attached storage (NAS) devices, other devices configured to store data in a persistent or non-persistent state, or a combination of different memory devices. In embodiments of the invention, memory 404 may comprise a non-transitory storage medium storing instructions that, when executed by one or more processors 401, cause one or more processors 401 to perform operations for analyzing, controlling, or both, dehydrogenating a hydrocarbon by one or more fixed bed reactors of a fixed bed dehydrogenation unit. In embodiments of the invention, the operations may include those shown in FIG. 2.

The operations described above as performed by a controller may be performed by any circuit configured to perform the described operations. Such a circuit may be an integrated circuit (IC) constructed on a semiconductor substrate and include logic circuitry, such as transistors configured as logic gates, and memory circuitry, such as transistors and capacitors configured as dynamic random access memory (DRAM), electronically programmable read-only memory (EPROM), or other memory devices. The logic circuitry may be configured through hard-wire connections or through programming by instructions contained in firmware. Further, the logic circuity may be configured as a general-purpose processor capable of executing instructions contained in software and/or firmware.

If implemented in firmware and/or software, functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise random access memory (RAM), read-only memory (ROM), electrically-erasable programmable read-only memory (EEPROM), compact disc read-only memory (CD-ROM) or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

CFD simulations were carried out for conventional sequencing and showed air and hydrocarbon flow distribution differences up to 7% between reactors. When sequenced with embodiments of the invention described herein, the CFD simulations predicted hydrocarbon flow differences of less than 0.5%.

What is claimed is:

1. A method of performing a fixed bed dehydrogenation process for producing olefins, the method comprising:
controlling at least three fixed bed dehydrogenation reactors configured to dehydrogenate a hydrocarbon to produce an olefin, wherein the controlling is performed such that a farthest two of the reactors, by distance, from each other are not operated simultaneously in either of dehydrogenation processing and catalyst regeneration processing.

2. The method of claim 1, wherein two or more of the reactors are allowed to be in the dehydrogenation processing and catalyst regeneration processing phases in parallel, as long as the two farthest reactors are not in parallel.

3. The method of claim 1, wherein the number of reactors is 3, 4, 5, 8, or 10.

4. The method of claim 1, wherein the dehydrogenation processing is a propane dehydrogenation process.

5. The method of claim 4, wherein the number of reactors are 8 or 10.

6. The method of claim 1, wherein the dehydrogenation processing is an isobutane dehydrogenation process, a n-butane to butene-1 dehydrogenation process, or a butadiene or isopentane dehydrogenation process.

7. The method of claim 6, wherein the number of reactors are 3, 4, or 5.

8. The method of claim 1, wherein the method is performed without heat generating inerts.

9. The method of claim 1, wherein the method is performed without CuO-α alumina.

10. The method of claim 1, wherein operation of the process results in Houdry lumps of 3000 kg or less, or alternatively 2500 kg or less, or alternatively about 500 kg to 2000 kg.

11. The method of claim 1, wherein the size of Houdry lumps formed in the at least three fixed bed dehydrogenation reactors are reduced compared to a method of controlling that is performed such that the farthest two reactors, by distance, from each other are operated simultaneously in either of dehydrogenation processing and catalyst regeneration processing.

12. The method of claim 1, wherein the number of reactors is 3, 4, 5, 8, or 10.

13. The method of claim 1, wherein the dehydrogenation processing is a propane dehydrogenation process.

14. The method of claim 13, wherein the number of reactors are 8 or 10.

15. The method of claim 1, wherein the dehydrogenation processing is an isobutane dehydrogenation process, a n-butane to butene-1 dehydrogenation process, or a butadiene or isopentane dehydrogenation process.

16. The method of claim 15, wherein the number of reactors are 3, 4, or 5.

17. The method of claim 1, wherein operation of the process results in Houdry lumps of 3000 kg or less, or alternatively 2500 kg or less, or alternatively about 500 kg to 2000 kg.

18. A programmable logic controller configured to perform the method of claim 1.

19. A method of performing a fixed bed dehydrogenation process for producing olefins, the method comprising:
controlling a multiple fixed bed adiabatic dehydrogenation based olefin manufacture system that comprises at least three fixed bed dehydrogenation reactors that are configured to share a feed source and configured to dehydrogenate a hydrocarbon to produce an olefin, wherein each of the at least three fixed bed dehydrogenation reactors comprise a catalyst bed that does not include a heat generating inert material, wherein the controlling is performed such that a farthest two of the reactors, by distance, from each other are not operated simultaneously in either of dehydrogenation processing and catalyst regeneration processing, and wherein the size of Houdry lumps formed in the at least three fixed bed dehydrogenation reactors are reduced compared to a method of controlling that is performed such that the farthest two reactors, by distance, from each other are operated simultaneously in either of dehydrogenation processing and catalyst regeneration processing.

20. The method of claim 19, wherein two or more of the reactors are allowed to be in the dehydrogenation processing and catalyst regeneration processing phases in parallel, as long as the two farthest reactors are not in parallel.

\* \* \* \* \*